US012708395B2

(12) United States Patent
Omar

(10) Patent No.: US 12,708,395 B2
(45) Date of Patent: Aug. 18, 2026

(54) DEVICES, SYSTEMS, AND METHODS FACILITATING FLUID-ASSISTED SURGICAL TISSUE TREATMENT

(71) Applicant: Medtronic Xomed, LLC, Jacksonville, FL (US)

(72) Inventor: Mansur I. Omar, Jacksonville, FL (US)

(73) Assignee: Medtronic Xomed, LLC, Jacksonville, FL (US)

( * ) Notice: Subject to any disclaimer, the term of this patent is extended or adjusted under 35 U.S.C. 154(b) by 733 days.

(21) Appl. No.: 18/114,029

(22) Filed: Feb. 24, 2023

(65) Prior Publication Data

US 2024/0016511 A1 Jan. 18, 2024

Related U.S. Application Data

(60) Provisional application No. 63/351,136, filed on Jun. 10, 2022.

(51) Int. Cl.
*A61B 17/32* (2006.01)
*A61B 17/00* (2006.01)

(52) U.S. Cl.
CPC .... *A61B 17/32* (2013.01); *A61B 2017/00075* (2013.01); *A61B 2017/00084* (2013.01); *A61B 2017/00115* (2013.01); *A61B 2017/00137* (2013.01); *A61B 2017/00199* (2013.01); *A61B 2017/00221* (2013.01);
(Continued)

(58) Field of Classification Search
CPC ........... A61B 2017/00017; A61B 2017/00022; A61B 2017/00221; A61B 2017/00199; A61B 2017/0046; A61B 2017/00477; A61B 2018/00178; H01R 13/005; H01R 2201/12
See application file for complete search history.

(56) References Cited

U.S. PATENT DOCUMENTS 6,626,355 B2 9/2003 Sasse et al.
7,214,038 B2 5/2007 Saxer et al.
(Continued)

FOREIGN PATENT DOCUMENTS

DE 10354147 A1 6/2005
DE 202017001894 U1 7/2017

OTHER PUBLICATIONS

Extended European Search Report issued in corresponding European Application No. 23176453.1 dated Oct. 18, 2023, 7 pages.

*Primary Examiner* — Deanna K Hall
(74) *Attorney, Agent, or Firm* — Carter, DeLuca & Farrell, LLP

(57) ABSTRACT

A surgical system includes a surgical end effector and a fluid and communication assembly. The surgical end effector is configured to releasably engage a surgical handpiece, includes electronics and a proximal hub having a connection port disposed thereon, and defines a fluid flow path. The fluid and communication assembly includes a cable and a connection plug disposed at a distal end portion of the cable. The cable includes a fluid line and a communication line. The connection plug is configured to releasably engage the connection port to thereby establish fluid communication between the fluid line and the fluid flow path and to thereby establish electrical communication between the communication line and the electronics.

18 Claims, 7 Drawing Sheets

(52) U.S. Cl.
CPC ................. *A61B 2017/0046* (2013.01); *A61B 2017/00982* (2013.01); *A61B 2017/320028* (2013.01); *A61B 2017/32004* (2013.01); *A61B 2217/005* (2013.01); *A61B 2217/007* (2013.01)

(56) References Cited

U.S. PATENT DOCUMENTS

| | | | |
|---|---|---|---|
| 7,238,010 | B2 | 7/2007 | Hershberger et al. |
| 7,258,534 | B2 | 8/2007 | Fathallah et al. |
| 7,632,079 | B2 | 12/2009 | Hershberger et al. |
| 7,901,376 | B2 | 3/2011 | Steck et al. |
| 8,070,712 | B2 | 12/2011 | Muri et al. |
| 8,142,397 | B2 | 3/2012 | Patzer |
| 8,539,672 | B2 | 9/2013 | Eggers |
| 8,591,453 | B2 | 11/2013 | Stubkjaer et al. |
| 8,663,157 | B2 | 3/2014 | Hacker et al. |
| 8,852,085 | B2 | 10/2014 | Shener-Irmakoglu et al. |
| 9,468,716 | B2 | 10/2016 | Hariharesan et al. |
| 9,603,990 | B2 | 3/2017 | Woolford |
| 9,770,541 | B2 | 9/2017 | Carr et al. |
| 9,889,246 | B2 | 2/2018 | Woolford |
| 10,265,217 | B2 | 4/2019 | Ross |
| 10,376,639 | B2 | 8/2019 | Magers et al. |
| 10,774,823 | B2 | 9/2020 | Loth et al. |
| 11,065,153 | B2 | 7/2021 | Muri et al. |
| 11,085,552 | B2 | 8/2021 | Moss et al. |
| 11,116,661 | B2 | 9/2021 | Muri et al. |
| 11,278,473 | B2 | 3/2022 | Elia et al. |
| 11,318,247 | B2 | 5/2022 | Buxton et al. |
| 11,348,674 | B2 | 5/2022 | Kamen et al. |
| 2008/0097284 | A1 | 4/2008 | Gao et al. |
| 2008/0281254 | A1* | 11/2008 | Humayun .............. A61B 90/98 604/22 |
| 2018/0236204 | A1 | 8/2018 | Milhous et al. |
| 2020/0038046 | A1 | 2/2020 | Schwamb et al. |
| 2020/0179576 | A1 | 6/2020 | Wood |
| 2021/0077689 | A1* | 3/2021 | Schenck ............... A61M 5/172 |
| 2022/0087730 | A1 | 3/2022 | Croft et al. |

* cited by examiner

DEVICES, SYSTEMS, AND METHODS FACILITATING FLUID-ASSISTED SURGICAL TISSUE TREATMENT

CROSS-REFERENCE TO RELATED APPLICATIONS

This application claims the benefit of, and priority to, U.S. Provisional Patent Application No. 63/351,136, filed on Jun. 10, 2022, the entire contents of which are hereby incorporated herein by reference.

FIELD

The present disclosure relates to surgical devices, systems, and methods and, more specifically, to powered, fluid-assisted surgical devices, systems, and methods.

BACKGROUND

Fluid is utilized in conjunction with many powered surgical devices, systems, and methods to facilitate performing a surgical task such as, for example, enabling irrigation at a treatment site, aspiration at a treatment site, cleaning of a surgical device, washing of a treatment site, clearing a field of view, cooling a surgical device, etc. Some non-limiting examples of surgical devices that may benefit from the use of fluid include microdebriders, surgical drills, surgical saws, suction irrigators, tissue shavers, endoscopes, balloon or other catheters, energy devices, and the like.

Powered surgical systems typically include a console connected to a surgical device to power and control the surgical device. Such consoles may further connect to a fluid source and/or fluid collection canister and incorporate a pump to enable control of the flow of fluid to and/or from the surgical site.

SUMMARY

The terms "about," substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is a surgical system including a surgical end effector and a fluid and communication assembly. The surgical end effector is configured to releasably engage a surgical handpiece, includes electronics and a proximal hub having a connection port disposed thereon, and defines a fluid flow path. The fluid and communication assembly includes a cable and a connection plug disposed at a distal end portion of the cable. The cable includes a fluid line and a communication line (e.g., for data and/or power transmission). The connection plug is configured to releasably engage the connection port to thereby establish fluid communication between the fluid line and the fluid flow path and to thereby establish electrical communication between the communication line and the electronics of the surgical end effector.

In an aspect of the present disclosure, the surgical system further includes the surgical handpiece. The surgical handpiece may include a motor configured to drive movement of a component of the surgical end effector. In these and other aspects, both the fluid communication between the fluid line and the fluid flow path and the electrical communication between the communication line and the electronics may be independent of the surgical handpiece.

In another aspect of the present disclosure, the fluid and communication assembly further includes a cassette disposed at a proximal end portion of cable. The cassette includes a cassette fluid line in fluid communication with the fluid line of the cable and a cassette communication line in electrical communication with the communication line of the cable.

In another aspect of the present disclosure, the cassette is configured to operably couple to a console for pumping fluid from the cassette fluid line, through the fluid line of the cable, through the connection plug, through the connection port, and to the fluid flow path of the surgical end effector. The cassette additionally or alternatively includes an electronics board configured to electrically communicate with the electronics of the surgical end effector via the cassette communication line, the communication line of the cable, the connection plug, and the connection port.

In still another aspect of the present disclosure, the electrical communication includes at least one of data or power signals. In aspects, the electrical communication includes both data and power signals.

In yet another aspect of the present disclosure, the electronics include at least one of: a memory, a processor, a sensor, or a user interface.

In still yet another aspect of the present disclosure, the electrical communication includes wireless electrical communication.

Another surgical system provided in accordance with aspects of the present disclosure includes a console, a surgical device including a handpiece and an end effector configured to releasably engage the handpiece, and a fluid and communication assembly. The handpiece includes a motor and is configured to connect to the console such that the console at least one of powers or controls the motor. The end effector includes a connection port, electronics, and defines a fluid flow path. The fluid and communication assembly includes a cable and a connection plug disposed at a distal end portion of the cable. The cable includes a fluid line and a communication line and is configured to operably couple to the console whereby the console is configured to pump fluid along the fluid line and electrically connect to the communication line. The connection plug is configured to releasably engage the connection port to thereby enable pumping of fluid through the fluid line (e.g., from a saline bag) to the fluid flow path and electrical communication between the console and the electronics. Further, in aspects, the fluid line and the electrical communication are electrically isolated from one another.

In an aspect of the present disclosure, the pumping of fluid from the fluid line to the fluid flow path and the electrical communication between the console and the electronics are independent of the handpiece.

In another aspect of the present disclosure, the fluid and communication assembly further includes a cassette disposed at a proximal end portion of cable. The cassette is configured to operably interface with the console. In aspects, the cassette includes an electronics board configured to electrically communicate with the electronics of the end effector via the communication line of the cable, the connection plug, and the connection port.

In still another aspect of the present disclosure, the electrical communication includes at least one of data or power signals. In aspects, the electrical communication includes both data and power signals.

In yet another aspect of the present disclosure, the electronics include at least one of: a memory, a processor, a sensor, or a user interface. With respect to at least one sensor of the electronics, the electronics may include a temperature sensor and/or a vibration sensor. With respect to the User Interface, the electronics may include one or more multi-color LED's, for example.

In still yet another aspect of the present disclosure, the connection plug is configured establish wireless electrical communication with the connection port.

In another aspect of the present disclosure, the console is configured to at least one of power or control the motor based on feedback from the electronics of the end effector received from the fluid and communication assembly independent of the handpiece.

BRIEF DESCRIPTION OF THE DRAWINGS

Various aspects and features of the present disclosure are described hereinbelow with reference to the drawings wherein.

DETAILED DESCRIPTION

Figures 1, 2:
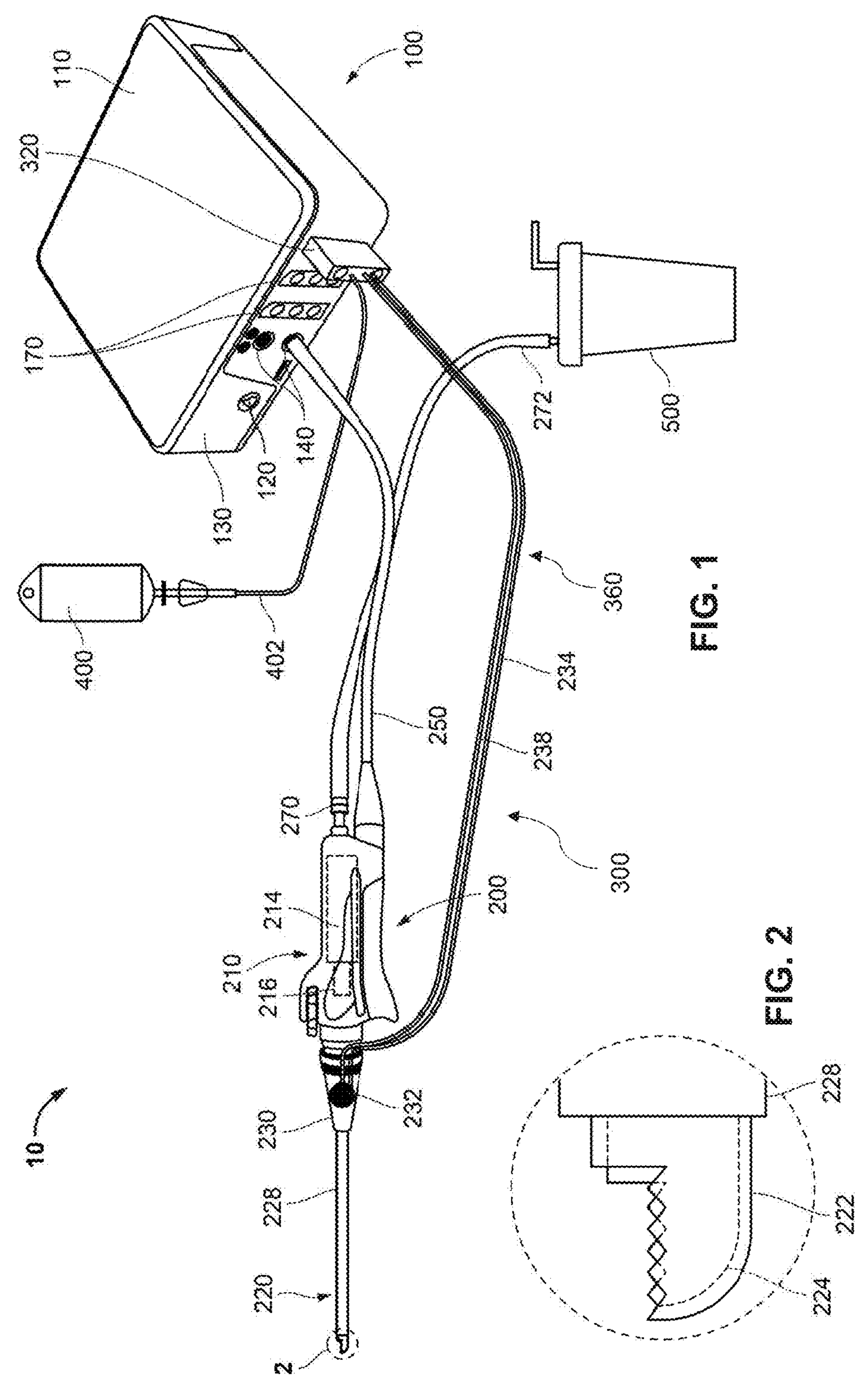
FIG. 1 is a perspective view of a surgical system provided in accordance with aspects of the present disclosure including a surgical device having a handpiece and an end effector, a console, and a fluid and communication assembly, wherein the surgical system is shown further including a fluid source and a fluid collection canister.
FIG. 2 is an enlarged, side view of the area of detail indicated as "2" in FIG. 1.

Referring to FIG. 1, a surgical system 10 provided in accordance with the present disclosure generally includes: a console 100; one or more surgical devices 200 configured to be powered, controlled, energized, supplied fluid, and/or supplied vacuum by console 100; one or more fluid and communication assemblies 300 each operably coupling console 100 with one of the surgical devices 200; one or more fluid sources 400; and/or one or more fluid collection canisters 500. Although plural surgical devices 200, fluid and communication assemblies 300, fluid sources 400, and/or fluid collection canisters 500 are contemplated, surgical system 10 is described below with reference to only one of each of these features for the purposes of brevity and understanding. Likewise, although console 100 may include plural identical or similar features to accommodate, for example, the plurality of surgical devices 200, fluid and communication assemblies 300, fluid sources 400, and/or fluid collection canisters 500, each of these features is described in the singular hereinbelow for the purposes of brevity and understanding.

Console 100 includes: a housing 110, a power button 120, a graphical user interface (GUI) 130 (such as, for example, a touch screen GUI), one or more ports 140, and a plurality of cassette bays 170. The one or more ports 140 may include, for example: one or more power ports for powering and controlling connected powered surgical device(s) e.g., surgical device 200; one or more energy ports for providing surgical energy, e.g., monopolar, bipolar, microwave, ultrasonic, thermal, light, and/or other surgical energy, to connected energy device(s); and/or one or more additional ports for connection of one or more auxiliary devices such as a foot switch. Console 100 further includes one or more central processing units (CPU's) and/or microcontroller units (MCU's), power generating and control hardware, surgical energy generating and control hardware, and/or any other suitable hardware and corresponding firmware/software stored thereon for operating and controlling operation of surgical devices 200 connected thereto.

Figure 4:
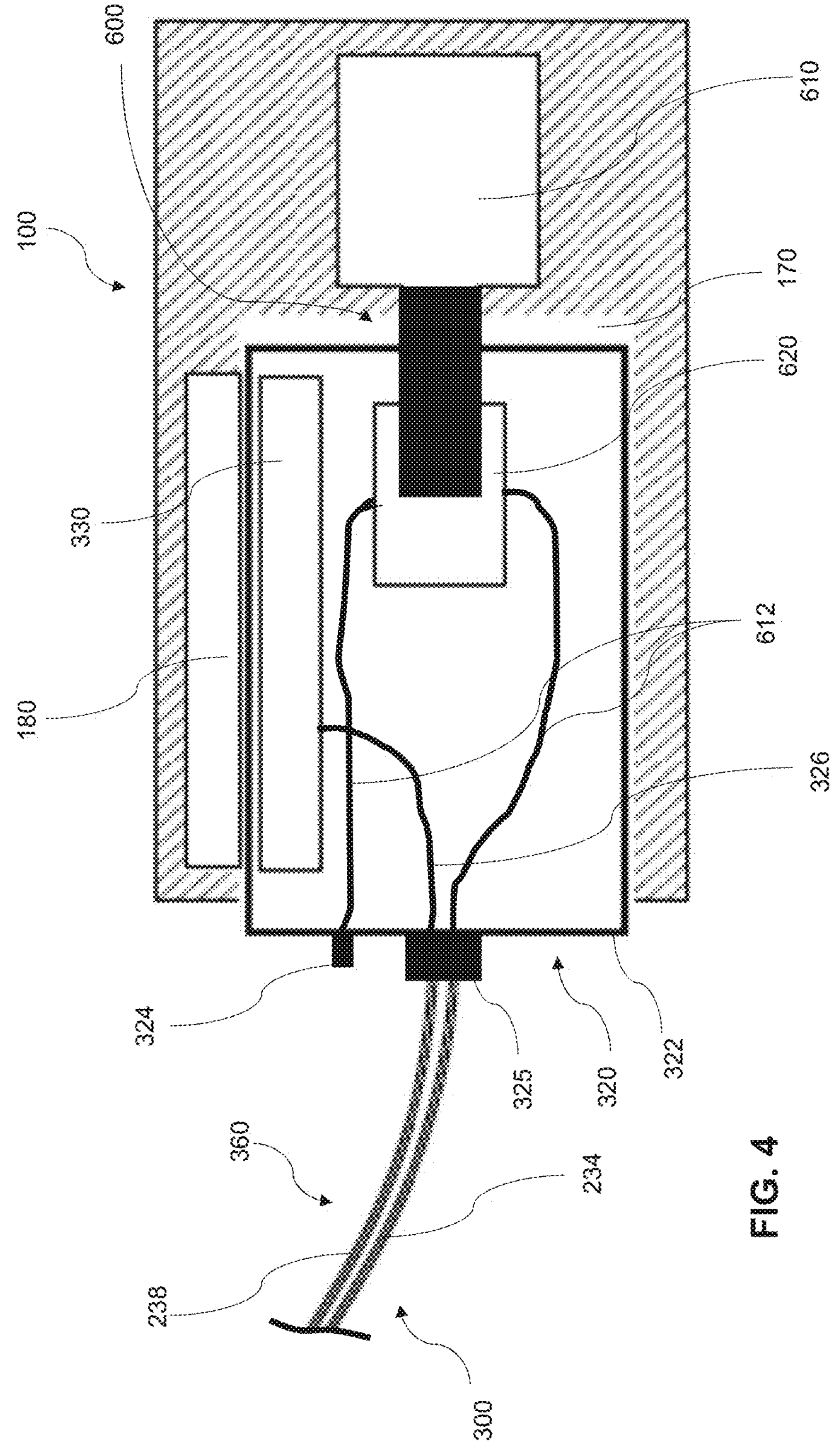
FIG. 4 is a schematic diagram illustrating a fluid cassette of the fluid and communication assembly interfacing with the console.

With momentary reference to FIG. 4, in conjunction with FIG. 1, console 100 additionally includes a first portion 610 of a pump 600 disposed therein and operably positioned relative to a corresponding cassette bay 170 to operably interface with a second portion 620 of pump 600 of cassette 320 of fluid and communication assembly 300 to enable the selective pumping of fluid through cassette 320 to selectively deliver fluid to surgical device 200 when cassette 320 is received within cassette bay 170. One of the CPU's and/or MCU's of console 100 may also control first portion 610 of pump 600 according to a particular control program selected (e.g., via GUI 130), according to user actuation of one or more user input controls, in response to sensed feedback, and/or in any other suitable manner.

Referring again to FIG. 1, surgical device 200, as noted above, may be powered, controlled, energized, supplied fluid, and/or supplied vacuum by console 100. Surgical device 200 may be configured as, for example and without limitation, one or more of a microdebrider, surgical drill, surgical saw, suction irrigator, tissue shaver, endoscope, sheath for an endoscope (e.g., a lens cleaning sheath), balloon or other catheter, energy device, fluid cooled device, etc.

In aspects, surgical device 200 includes a handpiece 210 and an end effector 220 releasably engagable with handpiece 210. More specifically, with respect to surgical tissue removal devices, e.g., microdebriders, surgical drills, tissue shavers, etc., handpiece 210 may include a motor 214 disposed therein and a drive rotor 216 coupled to motor 214 and configured to drive a movable (e.g., rotational, reciprocating, oscillating, or combinations thereof) component of end effector 220 to remove tissue from a surgical site. Handpiece 210 of surgical device 200 also include a power cord 250 configured to connect surgical device 200 to console 100, e.g., via one of ports 140 of console 100, to power and control motor 214, thereby controlling operation of end effector 220. Handpiece 210 of surgical device 200 may additionally include an internal outflow path fluidly coupled to end effector 220 and extending through handpiece 210 to an outflow port 270 to enable withdrawal of cut tissue (along with fluid and debris) from the surgical site via surgical device 200. Alternatively, the outflow path from end effector 220 may be external and/or independent of handpiece 210 (e.g., via an outflow port of proximal hub 230 of end effector 220) to inhibit tissue, fluid, and/or debris from contacting handpiece 210.

Figure 3:
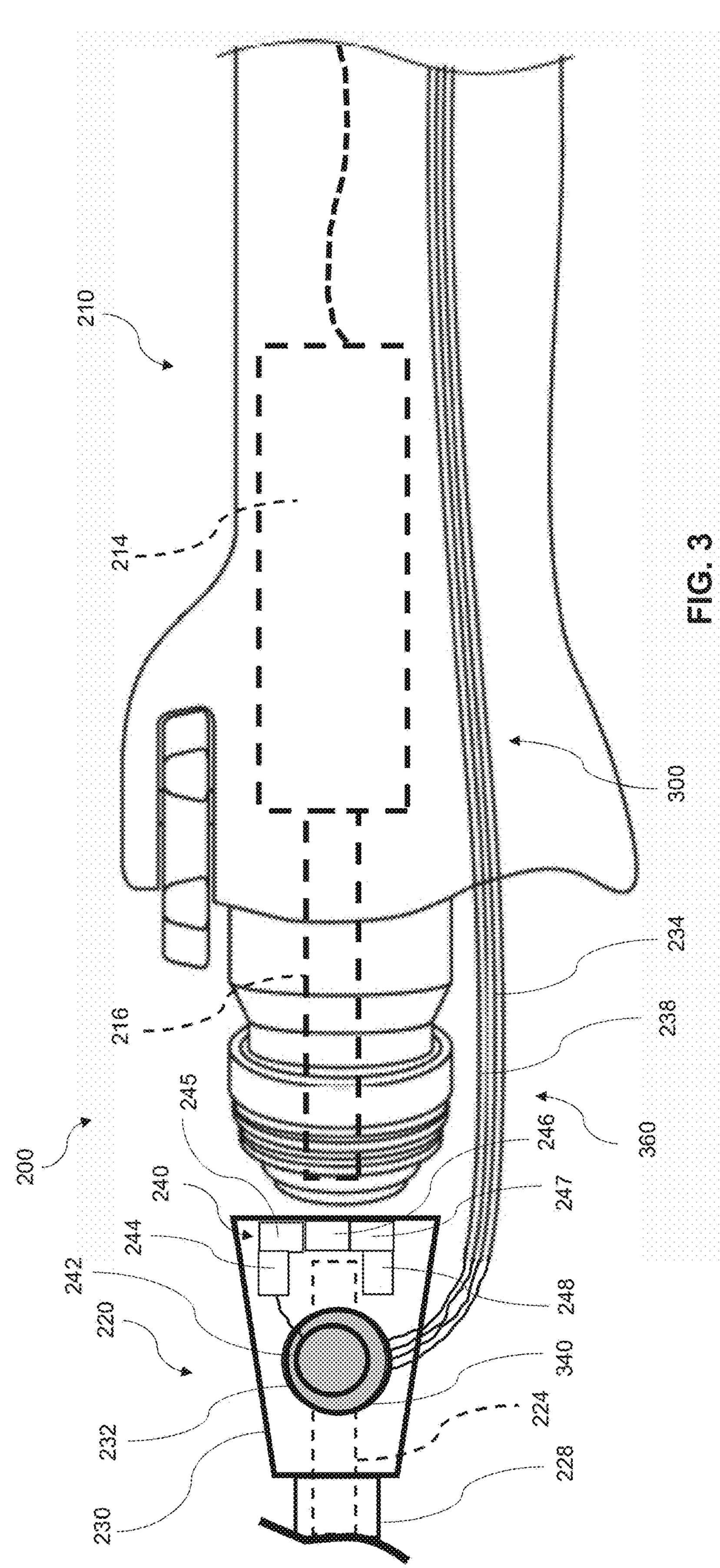
FIG. 3 is a perspective view illustrating the end effector of the surgical device disengaged from the handpiece of the surgical device with the fluid and communication assembly operably coupled to the end effector.

With additional reference to FIGS. 2 and 3, end effector 220 may include, for example, an outer shaft 222 and an inner shaft 224 configured to be driven by motor 214 via drive rotor 216 to move relative to outer shaft 222 to cut tissue. Further, vacuum may be applied through outer shaft 222 and/or inner shaft 224 to remove the cut tissue (along with fluid and debris) from the surgical site through outer shaft 222 and/or inner shaft 224 and to fluid collection canister 500. End effector 220 further include a sheath 228 disposed about outer shaft 222 and configured to deliver fluid to the surgical site, although in aspects sheath 228 is omitted and outer shaft 222 functions as the sheath to enable delivery of fluid therethrough and into a surgical site. Other suitable configurations of surgical device 200 for treating, e.g., cutting, shaving, boring, shaping, etc., tissue are also contemplated.

A proximal hub 230 configured to releasably engage end effector 220 with handpiece 210 is disposed at the proximal end of end effector 220. Proximal hub 230 may be fixed about proximal end portions of outer shaft 222 and/or sheath 228. Proximal hub 230 operably receives a proximal end portion of inner shaft 224 therein. More specifically, an internal drive coupler (not shown) disposed within proximal hub 230 may be provided to releasably operably couple inner shaft 224 of end effector 220 with drive rotor 216 of motor 214 of handpiece 210 when end effector 220 is engaged with handpiece 210, e.g., such that rotation of drive rotor 216 drives movement of inner shaft 224. Proximal hub 230 and handpiece 210 may include any suitable features to facilitate their releasable engagement such as, for example, complementary threading, male and female snap-fit components, etc.

Proximal hub 230 of end effector 220 further includes a connection port 232 to connect to an inflow fluid line 234 of fluid and communication assembly 300 and a communication line 238 of fluid and communication assembly 300 via a connection plug 340 of fluid and communication assembly 300. Connection of inflow fluid line 234 (e.g., tubing) with connection port 232 of proximal hub 230 allows fluid to be pumped through sheath 228 and into the surgical site. Additionally or alternatively, connection port 232 may enable connection of a vacuum line such that sheath 228 may be used for withdrawing fluid from the surgical site. Connection of communication line 238 (e.g., one or more electrical wires) with connection port 232 of proximal hub 230 enables power and data transmission between console 100 and proximal hub 230 of end effector 220 independently of handpiece 210 and any connections between handpiece 210 and console 100. Connection port 232 and fluid and communication assembly 300 are described in greater detail below. Other suitable configurations of surgical device 200 for fluid supply/removal are also contemplated.

Proximal hub 230 of end effector 220 also includes electronics 240 some or all of which may be disposed on a circuit board or otherwise arranged on or within proximal hub 230. Electronics 240 may include: a communication interface 242 operably positioned relative to connection port 232 and configured as, for example, a wireless antenna (for wireless data and power transmission) or a set of contacts (for wired data and power transmission); one or more memories 244 such as, for example, a Static Random-Access Memory (SRAM), an EEPROM, RFID tag and/or other suitable memory(s) 244 which may be configured as read-only or read/write memories (in aspects, a first memory is read only and a second memory is read/write capable); a processor 245, e.g., a microcontroller with associated memory; a power management unit 246; one or more sensors 247 such as, for example, a temperature sensor, e.g., a thermocouple, configured to measure a temperature of end effector 220; and/or a vibration or inertial sensor configured to measure vibrations, a vibration signature, orientation, and/or movement of end effector 220; and/or a user interface (UI) 248 such as, for example, one or more multi-color LED's configured to provide visual feedback to the user. In aspects, some or all of the one or more sensors 247 are not disposed at proximal hub 230 but are disposed at other locations of end effector 220, e.g., at a distal end portion thereof, and electrically coupled to the other electronics 240 via wired or wireless connections.

Referring back to FIG. 1, fluid source 400, e.g., an IV fluid bag, is fluidly coupled to one or more fluid flow paths defined within cassette 320 of fluid and communication assembly 300, e.g., via a fluid line 402 connected to one of one or more inflow ports 324 of cassette 320. Cassette 320 further includes one or more output ports 325 to enable fluid line 234 to connect the outflow of cassette 320 to connection port 232 of proximal hub 230 of end effector 220 of surgical device 200 to enable the supply of fluid to (or withdrawal of fluid from) sheath 228. Cassette 320 and console 100, as noted above, cooperate to define a pump 600 (FIG. 4) to enable the pumping of fluid from fluid source 400 to end effector 220 of surgical device 200 when cassette 320 is received within cassette bay 170 of console 100. As described in greater detail below, and as noted above, power and data transmission between console 100 and proximal hub 230 of end effector 220 independently of handpiece 210 is enabled via fluid and communication assembly 300.

Fluid collection canister 500, in aspects where provided, is fluidly coupled to outflow port 270 (or other suitable outflow port) of surgical device 200 via a fluid line 272 (e.g., tubing) and, in aspects, is further coupled to a vacuum source to facilitate the withdrawal of fluid (and tissue, debris, etc.) from the surgical site, through at least a portion of surgical device 200 (e.g., through only end effector 220 or through end effector 220 and handpiece 210), and into fluid collection canister 500.

Referring generally to FIGS. 1 and 2, in aspects, handpiece 210 of surgical device 200 is configured as a reusable component capable of being wiped down, sterilized, and/or otherwise cleaned for repeated use at the end-user, while end effector 220 of surgical device 200 is configured as a single-use component that is discarded after use or sent to a manufacturer for reprocessing. End effector 220, as noted above, is configured to releasably engage handpiece 210, thus facilitating disposal/reprocessing of end effector 220 and sterilization and/or other cleaning of handpiece 210 for subsequent use. Further, the releasable engagement of end effector 220 with handpiece 210 allows for interchangeable use of a variety of different end effectors 220 with handpiece 210.

Handpiece 210 is suitable for being configured as a reusable component because handpiece 210 can be made robust to withstand a significant number of uses, is not likely to wear over the course of its useful life, and because handpiece 210 includes relatively expensive capital equipment, e.g., motor 214. In order to enable efficient and effective cleaning of handpiece 210 for safe reuse of handpiece 210, certain features of surgical device 200 can be provided as part of and/or can be connected to end effector 220 independently of handpiece 210, thereby eliminating any challenges in incorporating such features into handpiece 210 without comprising the cleanability of handpiece 210 in preparation for subsequent use. For example: fluid inflow (and/or outflow) can be provided between console 100 and end effector 220 independently of handpiece 210; data and power communication (e.g., for authentication, exchange of operating parameters, etc.) can be provided between console 100 and end effector 220 independently of handpiece 210; one or more sensors 247 (FIG. 3) can be provided on end effector 220 and communication therewith can be provided between console 100 and end effector 220 independently of handpiece 210; and/or UI 248 (FIG. 3) can be provided on end effector 220 to enable console 100 to convey information to the user and/or receive information from the user via end effector 220 independently of handpiece 210. Console 100, fluid and communication assembly 300, and end effector 220 are configured to enable these features, as detailed below.

With reference to FIGS. 3 and 4, in conjunction with FIG. 1, fluid and communication assembly 300 includes a cassette 320 configured for releasable receipt within one of the cassette bays 170 of console 100, a connection plug 340 configured to connect to connection port 232 of end effector 220, and a cable 360 (including fluid line 234 and communication line 238, which are bundled along at least portions of the lengths thereof, e.g., adhered to one another, disposed within a common sheath, etc.) connecting cassette 320 and connection plug 340 with one another. Connection plug 340 is integrally engaged with a distal end portion of cable 360 and may be integrally engaged with connection port 232 of end effector 220 or may be configured to releasably connect to connection port 232 of end effector 220. A proximal end portion of cable 360 may be integrally connected to an output port 325 of cassette 320 or may be releasably engagable therewith.

Cassette 320 includes an outer housing 322 housing the internal operable components of cassette 320 therein including one or more fluid lines 612 (e.g., tubing), second portion 620 of pump 600, an electronics circuit board 330, and an electrical line 326 (e.g., including one or more electrical wires). Further, outer housing 322 includes one or more inflow ports 324 to enable connection of fluid source 400, e.g., via a fluid line 402, with the one or more of fluid lines 612; and one or more output ports 325 to enable connection of the one or more fluid lines 612 with corresponding fluid lines, e.g., inflow fluid line 234 of cable 360, to enable pump 600 to pump fluid along the one or more fluid lines 612 and through fluid line 234 of cable 360 to end effector 220 of surgical device 200. Electrical line 326 is also coupled to output port 325 to connect electronics circuit board 330 with cable 360, e.g., communication line 238 thereof. Electronics board 330 is configured to interface with an electronics board 180 of cassette bay 170 of console 100, e.g., via wireless or wired connection.

Console 100 includes first portion 610 of pump 600 (as noted above) disposed in electrical communication with electronics board 180. First portion 610 of pump 600, together with second portion 620 of pump 600, as detailed above, enables the pumping of fluid along the one or more fluid lines 612 from cassette 320 to end effector 220 of surgical device 200. First portion 610 of pump 600 may include, for example, pump drive hardware e.g., a stepper motor, and drive train configured to operably interface with a complementarily positioned peristaltic pump head and fluid line 612 (thus defining second portion 620 of pump 600) of cassette 320 such that first and second portions 610, 620 cooperate to define a peristaltic pump. In peristaltic pump configurations, the fluid line 612 that interfaces with the peristaltic pump head may be divided downstream of the peristaltic pump to provide multiple fluid lines 612 for selective and independent output of pumped fluid.

In other configurations, first portion 610 may include a pump drive actuator, e.g., a rotary actuator, configured to drive a pump head having one or more fluid lines 612 of cassette 320 connected thereto (thus defining second portion 620 of pump 600) such that portions 610, 620 cooperate to define a rotary pump. In these and other aspects where multiple fluid lines 612 (or multiple outputs from a divided fluid line 612) are provided, first portion 610 of pump 600 may include one or more valve actuators (e.g., solenoid driven valve actuators), to enable the fluid lines 612 to be selectively and independently pinched closed, thereby selectively and independently controlling fluid flow along multiple flow paths. Such a configuration suitable for use in accordance with the present disclosure is detailed in U.S. patent application Ser. No. 17/549,758, filed on Dec. 13, 2021 and titled "SURGICAL DEVICES, SYSTEMS, AND METHODS FACILITATING MULTIPLE FLOW PATH FLUID MANAGEMENT," the entire contents of which are hereby incorporated herein by reference. Other suitable configurations of pump 600 are also contemplated. Further, regardless of the particular configuration of pump 600, pump 600 enables the selective pumping of fluid from the fluid source 400 to end effector 220 of surgical device 200 (and/or otherwise to/from a surgical site and/or other surgical devices) via cassette 320.

Figure 6:
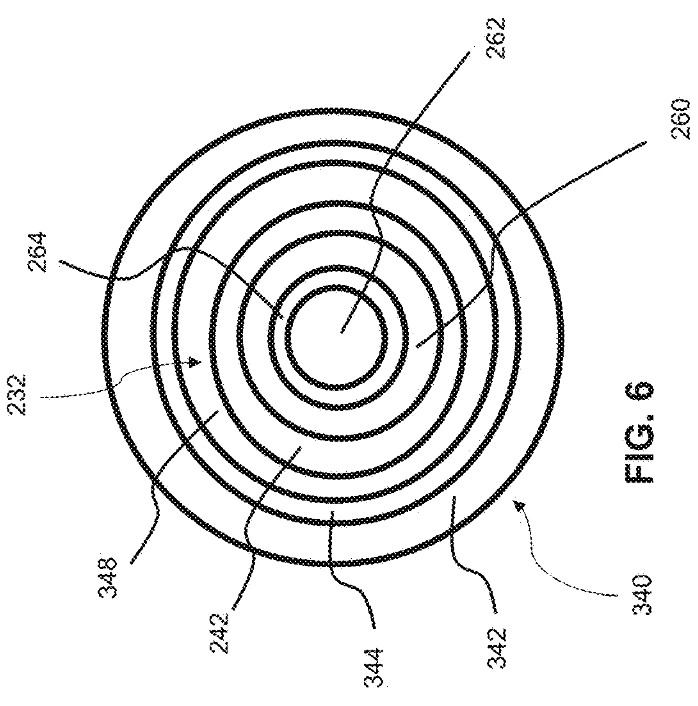
FIG. 6 is a transverse, cross-sectional view taken along section line "6-6" of FIG. 5.
Figure 5:
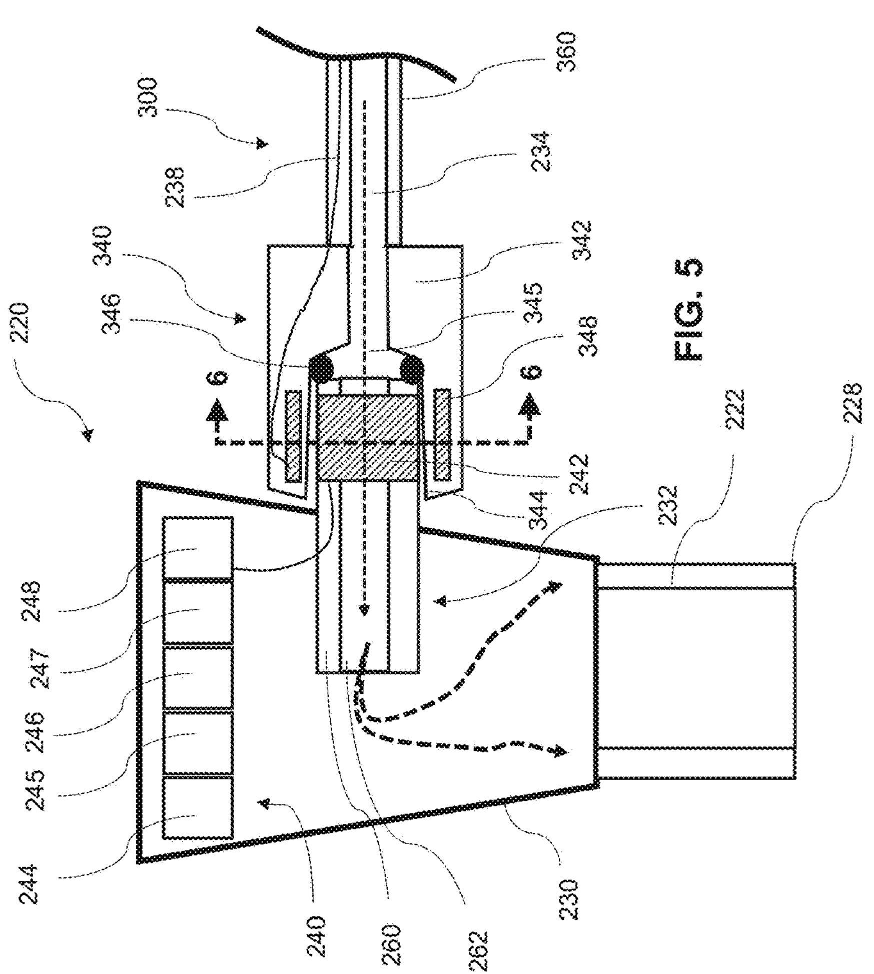
FIG. 5 is a longitudinal, cross-sectional view illustrating connection of the fluid and communication assembly with the end effector of the surgical device via a wireless connection.

Turning to FIGS. 5 and 6, in aspects, connection port 232 of proximal hub 230 of end effector 220 and connection plug 340 of fluid and communication assembly 300 are configured to wirelessly interface with one another to enable power and data communications, while at the same time operably couple with one another to permit the inflow of fluid into (and/or the outflow of fluid from) end effector 220. Connection port 232 defines a male body 260 including a lumen 262 defined therethrough. Lumen 262 is disposed in fluid communication with the annular space defined between outer shaft 222 and sheath 228 of end effector 220 and/or any other fluid-conveying passage defined through end effector 220 such that fluid pumped into lumen 262 can be delivered through end effector 220 to the surgical site (or withdrawn from the surgical site in the opposite manner). Connection port 232 further includes communication interface 242 extending about at least a portion of an outer perimeter of male body 260. Communication interface 242, more specifically, may be configured as an RFID antenna, an NFC antenna, or other suitable wireless communication interface. Communication interface 242 is connected to the other electronics 240 of proximal hub 230 of end effector 220, e.g., the one or more memories 244, processor 245, power management unit 246, one or more sensors 247, and UI 248. Further, male body 260 may be formed from an electrically insulative material and/or include an electrically insulative layer 264 (FIG. 6) disposed between lumen 262 and communication interface 242.

Connection plug 340 of fluid and communication assembly 300 defines a female body 342 including a recess 344 configured to receive male body 260 of connection port 232 of proximal hub 230 of end effector 220. Connection plug 340 further includes a mouth 345 establishing fluid communication between inflow fluid line 234 of cable 360 and the recess 344 of body 342. A seal 346, e.g., an O-ring, a gasket, etc., disposed within recess 344 is configured to establish a fluid-tight seal about the exterior perimeter of male body 260 of connection port 232 when male body 260 is received within recess 344 of female body 342 to thereby define a fluid flow path between inflow fluid line 234 of cable 360 and lumen 262 of connection port 232 when male body 260 is received within recess 344 of female body 342 that is sealed to inhibit fluid leakage. Connection plug 340 further includes a wireless communication interface 348, e.g., an RFID antenna, an NFC antenna, or other suitable wireless communication interface, disposed within female body 342 and extending about at least a portion of recess 344 such that, with male body 260 received within recess 344 of female body 342, wireless communication interface 348 and communication interface 242 are sufficiently aligned with one another to enable wireless data and/or power transmission therebetween. Wireless communication interface 348 is connected to communication line 238 of cable 360 such that, when connection plug 340 is engaged about connection port 232 (e.g., wherein male body 260 is sufficiently received within recess 344 of female body 342), data and/or power signals may be transmitted between console 100 (FIG. 4) and electronics 240 of end effector 220 via cassette 320 (FIG. 4), cable 360, and wireless communication interfaces 242, 348.

Referring to FIGS. 1 and 3-6, fluid flow from fluid source 400 to end effector 220 (e.g., for delivery to a surgical site) via fluid and communication assembly 300 is described. It is understood that fluid removal from the surgical site may be accomplished in the opposite manner and, thus, is not described hereinbelow. In order to enable fluid delivery to the surgical site, cassette 320 of fluid and communication assembly 300 is loaded into cassette bay 170 of console 100 to enable operable coupling of pump portions 610, 620 of console 100 and cassette 320, respectively, with one another to form pump 600; end effector 220 of surgical device 200 is engaged with handpiece 210 of surgical device 200; and connection plug 340 of fluid and communication assembly 300 is engaged about connection port 232 of end effector 220. Further, fluid line 402 is connected between fluid source 400 and one of the inflow ports 324 of cassette 320. With these connections established, pump 600 can be driven to pump fluid from fluid source 400 through fluid line 402, from fluid line 402 through inflow port 324 of cassette 320 into fluid line 612 of cassette 320 (a portion of which interfaces with pump 600, thus enabling the pumping of fluid therethrough), from fluid line 612 through one of the output ports 325 into inflow fluid line 234 of cable 360, through inflow fluid line 234 into mouth 345 of connector plug 340, from mouth 345 into lumen 262 of connection port 232 of end effector 220, and from lumen 262 through end effector 220 into the surgical site.

Figure 7:
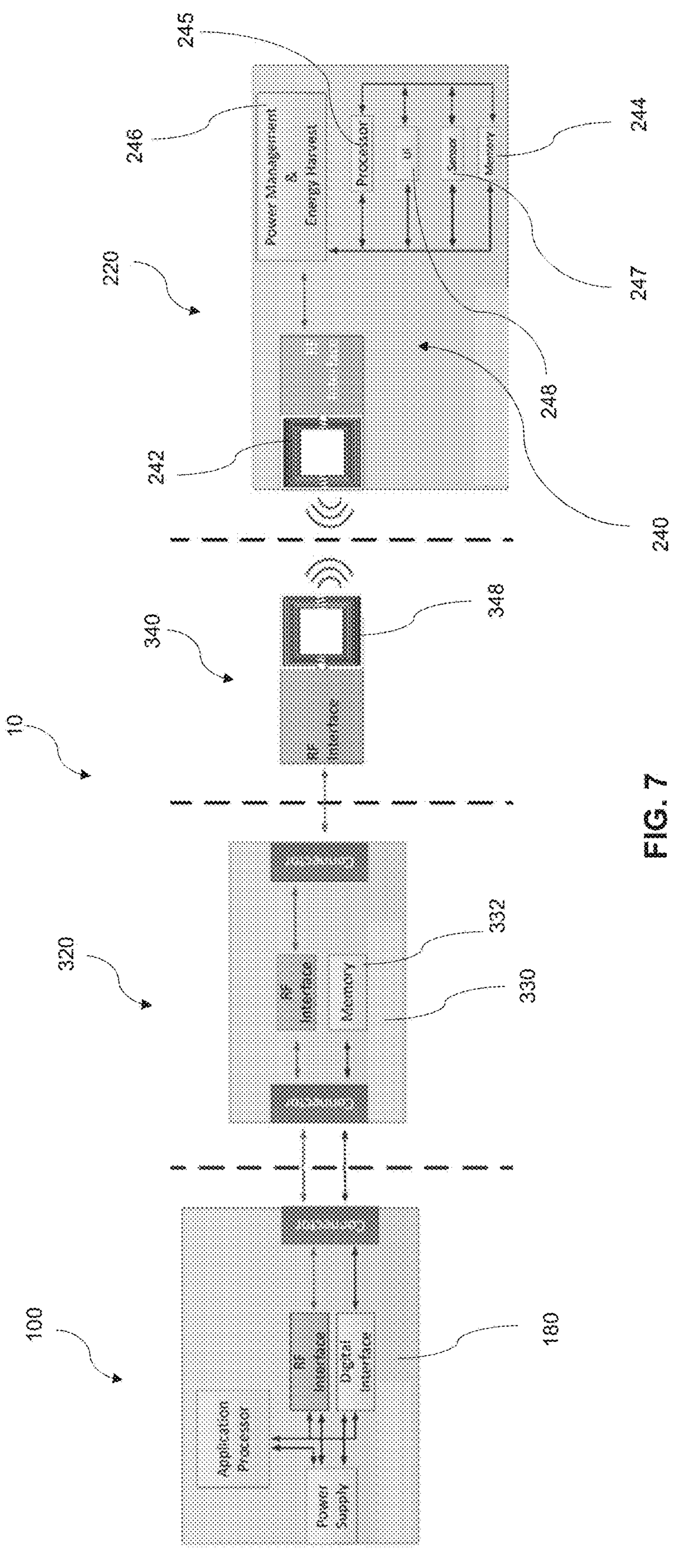
FIG. 7 is a block diagram illustrating wireless communication between the console and the end effector of the surgical device via the fluid and communication assembly.

Also referring to FIG. 7, power and data communication between console 100 and end effector 220 via fluid and communication assembly 300 is described. In order to enable power and data communication between console 100 and end effector 220, cassette 320 of fluid and communication assembly 300 is loaded into cassette bay 170 of console 100 to enable electronics board 330 of cassette 320 to interface (e.g., via wireless or wired connection) with electronics board 180 of cassette bay 170 of console 100; end effector 220 of surgical device 200 is engaged with handpiece 210 of surgical device 200; and connection plug 340 of fluid and communication assembly 300 is engaged about connection port 232 of end effector 220 to thereby sufficiently approximate wireless communication interfaces 242, 348 of end effector 220 and connection plug 340 of fluid and communication assembly 300.

Once the above connections are established, console 100 may direct power and/or data signals from electronics board 180 for wired or wireless transmission to electronics board 330 of cassette 320. Electronics board 330 of cassette 320, in turn, communicates power and/or data signals to communication line 238 of cable 360, via electrical line 326 and output port 325. Communication line 238 of cable 360 transmits the power and/or data signals to wireless communication interface 348 of connection plug 340 which wirelessly transmits power and/or data signals to wireless communication interface 242 of connection port 232 of end effector 220. As noted above, wireless communication interface 242 is connected to the other electronics 240 of end effector 220. Thus, communication of power and/or data signals between console and end effector 220 is enabled.

With respect to power signals, RF power may be transmitted from an RF power supply associated with electronics board 180 of console 100, through electronics board 330 of cassette 320, communication line 238 of cable 360, wireless communication interfaces 348, 242, and to power management unit 246 of electronics 240 of end effector 220. Power management unit 246 is configured to harvest energy from the RF power signal and mange power distribution to the various other electronics 240 of end effector 220. For example, power management unit 246 may power, based on the RF power signal received from console 100, communication interface 242 (where communication interface 242 is active rather than passive), the one or more memories 244 (where the one or more memories 244 are active rather than passive), processor 245, the one or more sensors 247, and/or UI 248.

Data communication may be bi-directional. That is, data signals may be transmitted from electronics board 180 of console 100, through electronics board 330 of cassette 320, communication line 238 of cable 360, wireless communication interfaces 348, 242, and to processor 245 of electronics 240 of end effector 220, and from processor 245 of electronics 240 of end effector 220, through wireless communication interfaces 348, 242, communication line 238 of cable 360, and electronics board 330 of cassette 320, to electronics board 180 of console 100.

Data communication between console 100 and end effector 220 may include console 100 accessing the one or more memories 244 of end effector 220 and/or writing information to the one or more memories 244. For example, a read-only memory of the one or more memories 244 may store identifying information associated with end effector 220 that can be read by console 100 (e.g., unique ID, device type, lot number, manufacture date, etc.). Other information associated with end effector 220, stored in a read-only memory of the one or more memories 244, and readable by console 100 may include configuration data, features, components, and/or settings associated with end effector 220 to facilitate configuring console 100 for use therewith (e.g., to drive motor 214 of handpiece 210 accordingly (see FIGS. 1 and 3); and/or to authenticate end effector 220 (e.g., to prevent counterfeit or unverified end effectors 220 from being used). Information may also be read/written to/from a read/write memory of the one or more memories 244 of end effector 220; such information may include, for example, a use count, usage information, a use flag indicating that end effector 220 has been used, an error log, etc.

In aspects, console 100 may also communicate with one or more memories 332 of electronics board 330 of cassette 320 to read/write data to/from the one or more memories 332 of cassette 320 similarly as detailed above with respect to end effector 220 except that the information stored/read/written pertains to cassette 320 rather than end effector 220.

Data communication between console 100 and end effector 220 also enables feedback signals, e.g., based upon sensor data obtained from the one or more sensor 247 of end effector 220, to be communicated to console 100 to control the driving of motor 214 and/or operation of pump 600. For example, temperature data from a temperature sensor 247 may be communicated to console 100. Console 100, in turn, may control the driving of motor 214 of handpiece 210 based on the temperature data received. That is, motor 214 may be driven at a lower speed or may be stopped altogether in response to temperature data indicating that end effector 220 is above one or more threshold temperatures for the particular operating mode. Console 100 may additionally or alternatively take other action such as, for example: outputting an indicator (e.g., visual, audible, tactile, etc.) from console 100 and/or UI 248 of end effector 220 indicating that end effector 220 has exceeded one or more threshold temperatures; controlling pump 600 to activate or increase fluid flow to thereby facilitate cooling end effector 220; and/or other suitable actions.

Where one of the one or more sensors 247 is a vibration or inertial sensor, e.g., one or more accelerometers, gyroscopes, magnetometers, combinations thereof, etc., sensor data may be communicated to console 100 to enable console 100 to control the driving of motor 214 of handpiece 210 and/or control pump 600 based thereon. For example, where vibration above a threshold magnitude or an unusual vibration signature for the particular operating mode is detected, motor 214 may be driven at a lower speed or may be stopped altogether. Further, console 100 may output an indicator (e.g., visual, audible, tactile, etc.) from console 100 and/or UI 248 of end effector 220 indicating an error condition associated with the detected vibrations of end effector 220 (e.g., that end effector 200 is potentially damaged and is not operating properly, to check connection between end effector 220 and handpiece 210, that end effector 220 has contacted a foreign structure such as another surgical instrument, etc.) Other suitable actions based on vibrational or inertial sensor feedback are also contemplated.

Additionally or alternatively, vibrational or inertial sensor data may be communicated to console 100 to enable console 100 to track the orientation of end effector 220, movement of end effector 220 in 3D space, activation and deactivation of handpiece 210 (e.g., motor start/stop conditions), and/or the presence or absence of fluid flow through end effector 220. Based on this sensor data received at console 100, console 100 may confirm that handpiece 210 was activated and/or deactivated properly (e.g., by comparing the control signals output to surgical device 200 from console 100 with motor start/stop and/or fluid flow conditions detected). Additionally or alternatively, console 100 may determine which handpiece 210 among a plurality of handpieces is the active handpiece (e.g., based on accelerometer and/or gyroscope data indicating the moving surgical device 200) and correspondingly assign functions, auxiliary devices, fluid lines, etc. thereto while deactivating the inactive handpieces.

Such sensor data may also be utilized to determine an orientation of surgical device 200 from one or more predefined orientations, e.g., at or sufficiently close (within 10 degrees or within 20 degrees) to one of the predefined orientations. The predefined orientations may be set at manufacturing, may be user-settable, or may be determined in any other suitable manner. The predefined orientations may include, for example, a use orientation (wherein surgical device 200 is angled with the tip facing down, indicating active use), a change orientation (wherein surgical device 200 is vertically upwardly oriented, indicating an intent to change out a tool), or a standby orientation (wherein surgical device 200 is horizontally oriented indicating surgical device 200 is resting on a surgical tray). When the active mode is detected, console 100 may assign functions, auxiliary devices, fluid lines, etc. to surgical device 200. When the change mode is detected, console 100 may inhibit activation to protect the patient and clinicians. When the standby orientation is detected, console 100 may switch surgical device 200 to a safe mode to prevent inadvertent activation thereof.

Sensed data may additionally or alternatively be utilized to determine a trajectory of motion of surgical device 200, e.g., based upon tracking position and orientation as a function of time, and monitor the trajectory thereof. Once the trajectory of surgical device 200 is determined, further motion thereof is monitored and compared to the determined trajectory. If the further motion is aligned with the determined trajectory, sufficiently close to the determined trajectory (such as, for example, within a cone of deviation or other acceptable limits), or otherwise acceptable based on the determined trajectory, no output or a confirmatory output, e.g., at console 100 and/or UI 248, is provided. On the other hand, if the further motion sufficiently deviates from the determined trajectory or otherwise exceeds acceptable limits, a suitable output warning the clinician may be provided, e.g., at console 100 and/or UI 248.

Continuing with reference to FIGS. 1 and 3-7, data communication between console 100 and end effector 220 further enables console 100 to direct outputs via UI 248. For example, console 100 may signal processor 245 of electronics 240 to output a particular indicator via UI 248 corresponding to: the operating mode of surgical device 200, whether motor 214 is activated, whether fluid inflow or outflow is activated, whether an error condition has been detected, etc. As noted above, UI 248 may include one or more multi-color LED's configured to provide visual feedback to the user. Other suitable additional or alternative configurations of UI 248 are also contemplated such as, for example; a speaker or other audible output device; a vibration generator or other suitable tactile output device; and/or another visual output device such as a graphical user interface.

Figure 8:
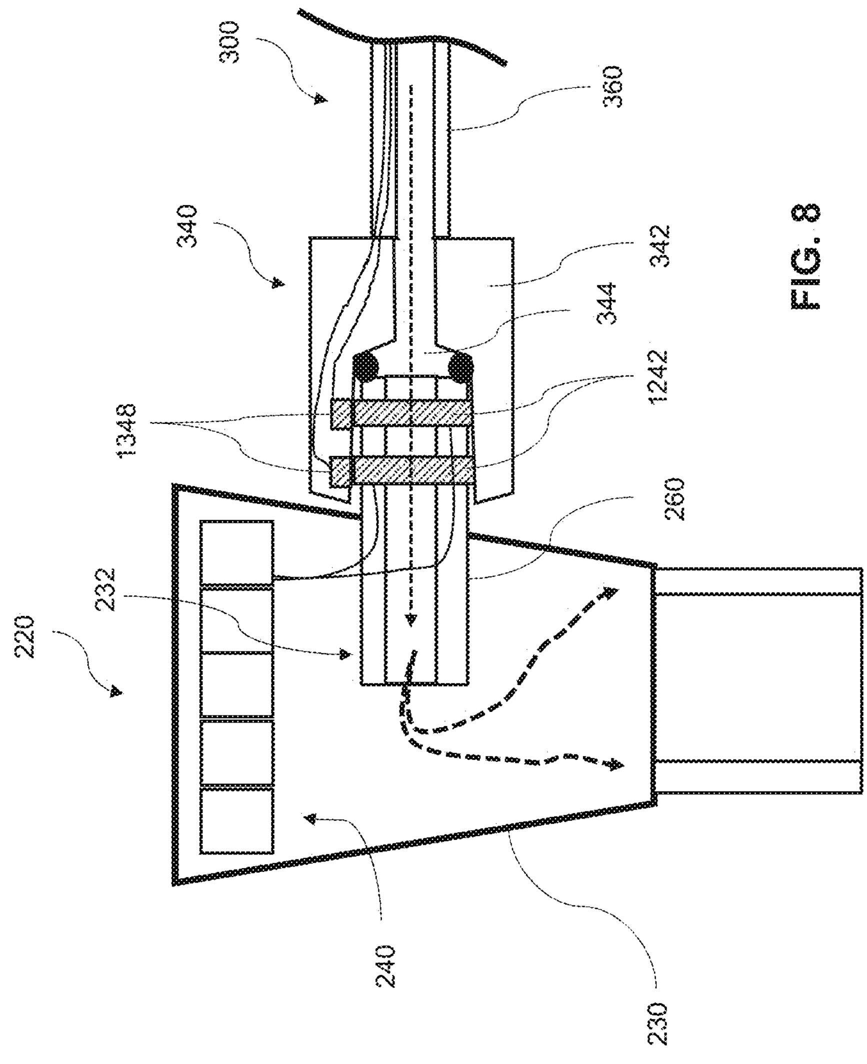
FIG. 8 is a longitudinal, cross-sectional view illustrating connection of the fluid and communication assembly with the end effector of the surgical device via a wired connection.
Figure 9:
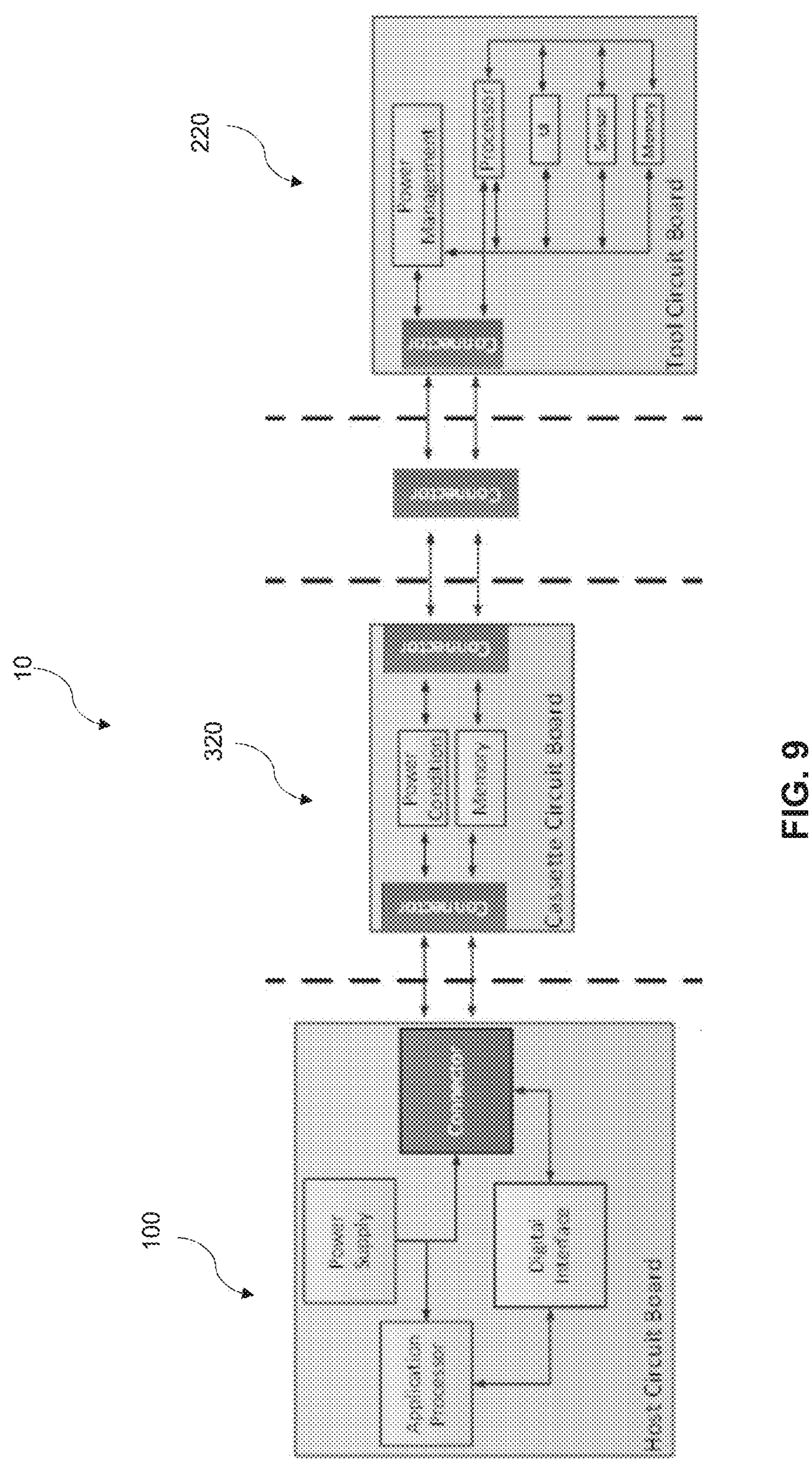
FIG. 9 is a block diagram illustrating wired communication between the console and the end effector of the surgical device via the fluid and communication assembly.

Turning to FIGS. 8-9, in aspects, rather than wireless communication, communication plug 340 of fluid and communication assembly 300 and end effector 220 may be configured for wired power and/or data communication. More specifically, in such configurations, rather than wireless communication interfaces enabling power and/or data transfer between connection port 232 of end effector 220 and connection plug 340 of fluid and communication assembly 300, connection port 232 may include a plurality of contact rings 1242 disposed about male body 260 of connection port 232 and operably connected to the other electronics 240 of end effector 220. In such configurations, connection plug 340 includes a plurality of contacts 1348 disposed within female body 342 and protruding into recess 344 such that, with male body 260 received within recess 344 of female body 342, corresponding pairs of contact rings 1242 and contacts 1348 mate with one another to enable contact-based data and/or power transmission therebetween. In aspects, both wired and wireless communications are enabled, e.g., power transmission via wired connection (see FIG. 8) and data transmission via wireless connection (see FIG. 5). Other suitable configurations are also contemplated.

Continuing with reference to FIG. 9, in such wired configurations as detailed above, cassette 320 of fluid and communication assembly 300 may be configured for wired communication, e.g., via cooperating contacts, with console 100. Alternatively, hybrid wired and wireless configurations are contemplated, e.g., wherein one of the communication between cassette 320 and console 100 or the communication between connection plug 340 and end effector 220 is wired and wherein the other of the communication between cassette 320 and console 100 or the communication between connection plug 340 and end effector 220 is wireless.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A surgical system, comprising:

a surgical handpiece having a power cable engaged therewith for delivering at least one of power or control signals to the surgical handpiece;

a surgical end effector configured to releasably engage the surgical handpiece, the surgical end effector including a proximal hub having a connection port disposed thereon, the surgical end effector including electronics and defining a fluid flow path; and a fluid and communication assembly including a cable and a connection plug disposed at a distal end portion of the cable, the cable including a fluid line and a communication line, wherein the connection plug is configured to releasably engage the connection port to thereby engage the cable with the proximal hub of the surgical end effector to establish fluid communication between the fluid line and the fluid flow path and to thereby establish electrical communication between the communication line and the electronics.

2. The surgical system according to claim 1, wherein the fluid and communication assembly further includes a cassette disposed at a proximal end portion of cable, the cassette including a cassette fluid line in fluid communication with the fluid line of the cable and a cassette communication line in electrical communication with the communication line of the cable.

3. The surgical system according to claim 2, wherein the cassette is configured to operably couple to a console for pumping fluid from the cassette fluid line, through the fluid line of the cable, through the connection plug, through the connection port, and to the fluid flow path of the surgical end effector.

4. The surgical system according to claim 2, wherein the cassette further includes an electronics board configured to electrically communicate with the electronics of the surgical end effector via the cassette communication line, the communication line of the cable, the connection plug, and the connection port.

5. The surgical system according to claim 1, wherein the electrical communication includes at least one of data or power signals.

6. The surgical system according to claim 1, wherein the electrical communication includes both data and power signals.

7. The surgical system according to claim 1, wherein the electronics include at least one of: a memory, a processor, a sensor, or a user interface.

8. The surgical system according to claim 1, wherein the electrical communication includes wireless electrical communication.

9. A surgical system, comprising:

a console;

a surgical device including a handpiece and an end effector configured to releasably engage the handpiece, the handpiece including a motor and having a power cable engaged therewith that is configured to connect to the console such that the console at least one of powers or controls the motor, the end effector including a connection port, electronics, and defining a fluid flow path; and a fluid and communication assembly including a cable and a connection plug disposed at a distal end portion of the cable, the cable including a fluid line and a communication line and configured to operably couple to the console whereby the console is configured to pump fluid along the fluid line and electrically connect to the communication line, wherein the connection plug is configured to releasably engage the connection port to thereby engage the cable with the end effector to enable pumping of fluid through the fluid line to the fluid flow path and electrical communication between the console and the electronics.

10. The surgical system according to claim 9, wherein the pumping of fluid from the fluid line to the fluid flow path and the electrical communication between the console and the electronics are independent of the handpiece.

11. The surgical system according to claim 9, wherein the fluid and communication assembly further includes a cassette disposed at a proximal end portion of cable, the cassette configured to operably interface with the console.

12. The surgical system according to claim 11, wherein the cassette includes an electronics board configured to electrically communicate with the electronics of the end effector via the communication line of the cable, the connection plug, and the connection port.

13. The surgical system according to claim 9, wherein the electrical communication includes at least one of data or power signals.

14. The surgical system according to claim 9, wherein the electrical communication includes both data and power signals.

15. The surgical system according to claim 9, wherein the electronics include at least one of: a memory, a processor, a sensor, or a user interface.

16. The surgical system according to claim 9, wherein the electronics includes at least one of a temperature sensor or a vibration sensor.

17. The surgical system according to claim 9, wherein the connection plug is configured establish wireless electrical communication with the connection port.

18. The surgical system according to claim 9, wherein the console is configured to at least one of power or control the motor based on feedback from the electronics of the end effector received from the fluid and communication assembly independent of the handpiece.

* * * * *